US011006888B2

(12) United States Patent
Pamula et al.

(10) Patent No.: US 11,006,888 B2
(45) Date of Patent: May 18, 2021

(54) SYSTEM AND METHOD FOR CUFFLESS BLOOD PRESSURE ESTIMATION

(71) Applicants: IMEC VZW, Leuven (BE); Katholieke Universiteit Leuven, KU LEUVEN R&D, Leuven (BE)

(72) Inventors: Venkata Rajesh Pamula, Leuven (BE); Marian Verhelst, Mechelen (BE)

(73) Assignee: IMEC vzw, Leuven (BE)

( * ) Notice: Subject to any disclaimer, the term of this patent is extended or adjusted under 35 U.S.C. 154(b) by 0 days.

(21) Appl. No.: 15/939,119

(22) Filed: Mar. 28, 2018

(65) Prior Publication Data
US 2018/0279898 A1    Oct. 4, 2018

(30) Foreign Application Priority Data

Mar. 28, 2017    (EP) ..................................... 17163211

(51) Int. Cl.
*A61B 5/346*     (2021.01)
*A61B 5/02*      (2006.01)
(Continued)

(52) U.S. Cl.
CPC ............ *A61B 5/366* (2021.01); *A61B 5/0245* (2013.01); *A61B 5/02108* (2013.01);
(Continued)

(58) Field of Classification Search
CPC . A61B 5/0472; A61B 5/0245; A61B 5/02108; A61B 5/0456; A61B 5/7278
See application file for complete search history.

(56) References Cited

U.S. PATENT DOCUMENTS

| | | | |
|---|---|---|---|
| 2009/0281399 A1* | 11/2009 | Keel .................. | A61B 5/02158 600/301 |
| 2010/0081946 A1* | 4/2010 | Garudadri ............ | A61B 5/0002 600/485 |

(Continued)

OTHER PUBLICATIONS

Zheng, Yali et al., "Wearable Cuff-less PTT-based System for Overnight Blood Pressure Monitoring", Engineering in Medicine and Biology Society (EMBS), 35th Annual International Conference of the IEEE EMBS, Osaka, Japan, Jul. 3-7, 2013, pp. 6103-6106.

(Continued)

*Primary Examiner* — Allen Porter
*Assistant Examiner* — Adreanne A. Arnold
(74) *Attorney, Agent, or Firm* — McDonnell Boehnen Hulbert & Berghoff LLP

(57) ABSTRACT

Disclosed is a system for estimating arterial blood pressure. The system includes a heartbeat detection module configured to receive an electrocardiogram signal, and detect one or more QRS complexes of the electrocardiogram signal. The system also includes a photoplethysmographic sensor module configured to trigger a light emitter, thereby generating a plurality of samples of a photoplethysmographic signal. Further, the system includes a blood pressure calculation module configured to receive information about the detected one or more QRS complexes and the plurality of photoplethysmographic signal samples, and calculate at least one blood pressure value based on a pulse arrival time period between the electrocardiogram and the photoplethysmographic signal. Additionally, the photoplethysmographic sensor module is further configured to receive information about the detected one or more QRS complexes, trigger, each time a QRS complex is detected, the generation of the plurality of photoplethysmographic signal samples, and (Continued)

determine a photoplethysmographic signal acquisition period.

19 Claims, 8 Drawing Sheets

(51) Int. Cl.
  *A61B 5/366* (2021.01)
  *A61B 5/024* (2006.01)
  *A61B 5/00* (2006.01)
  *A61B 5/021* (2006.01)
  *A61B 5/349* (2021.01)
  *A61B 5/352* (2021.01)
  *A61B 5/0245* (2006.01)

(52) U.S. Cl.
  CPC ...... *A61B 5/02125* (2013.01); *A61B 5/02416* (2013.01); *A61B 5/349* (2021.01); *A61B 5/352* (2021.01); *A61B 5/7285* (2013.01); *A61B 5/7278* (2013.01)

(56) References Cited

U.S. PATENT DOCUMENTS

2010/0324384 A1* 12/2010 Moon .................... A61B 5/746
  600/323
2012/0078131 A1* 3/2012 Zong ...................... A61B 5/746
  600/513
2013/0324809 A1* 12/2013 Lisogurski ........... A61B 5/7285
  600/323

OTHER PUBLICATIONS

Winokur, E.S. et al., "A Low-Power, Dual-Wavelength Photoplethysmogram (PPG) SoC With Static and Time-Varying Interferer Removal", IEEE Transactions on Biomedical Circuits and Systems, vol. 9, No. 4, Aug. 2015, pp. 581-589.
Poon, C.C.Y. et al., "Cuff-less and Noninvasive Measurements of Arterial Blood Pressure by Pulse Transit Time", Proceedings of the 2005 IEEE Engineering in Medicine and Biology 27th Annual Conference, Sep. 1-4, 2005, pp. 5877-5880.
Baheti, Pawan K. et al., "An Ultra Low Power Pulse Oximeter Sensor Based On Compressed Sensing", 2009 Sixth International Workshop on Wearable and Implantable Body Sensor Networks, Jun. 2009, pp. 144-148.
Pamula, V. Rajesh et al., "A 17nA, 47.2dB Dynamic Range, Adaptive Sampling Controller for Online Data Rate Reduction in Low Power ECG Systems", 2016 IEEE Biomedical Circuits and Systems Conference (BioCAS), Oct. 2016, pp. 272-275.
Extended European Search Report and Written Opinion, EP Application 18020124.6, dated Aug. 7, 2018, 8 pages.

* cited by examiner

SYSTEM AND METHOD FOR CUFFLESS BLOOD PRESSURE ESTIMATION

CROSS-REFERENCE TO RELATED APPLICATIONS

The present application is a non-provisional patent application claiming priority to European Patent Application No. EP 17163211.0, filed on Mar. 28, 2017, the contents of which are hereby incorporated by reference.

FIELD OF THE DISCLOSURE

The present description relates generally to electronic systems for arterial blood pressure estimation and more specifically to an electronic system, device, and method for non-invasive cuffless blood pressure estimation.

BACKGROUND

Continuous and non-invasive estimation of arterial blood pressure (BP) without using a cuff has gained emerging interest for health care applications. Instead of commonly used cuff-based measurements, changes in the Pulse Wave Velocity (PWV), i.e., the speed of a pressure pulse propagating along the arterial wall, can be an alternative approach for a continuous, non-invasive, and indirect BP measurement. As a surrogate of PWV, an indirect estimation of BP can be also obtained with the use of Pulse Transit Time (PTT) or Pulse Arrival Time (PAT), as for example described in "*Wearable Cuff-less PTT-based System for Overnight Blood Pressure Monitoring*", by Yali Zheng et al., Engineering in Medicine and Biology Society (EMBS), 35th Annual International Conference of the IEEE EMBS, pp. 6103-6106, Osaka 3-7 July 2013, in "*A low-power, dual-wavelength photoplethysmogram (PPG) SoC with static and time-varying interferer removal*" by E. S. Winokur et al., IEEE Transactions on Biomedical Circuits and Systems, vol. 9, no. 4, pp. 581-589, 2015, in "*Cuff-less and noninvasive measurements of arterial blood pressure by pulse transit time*" by C. Poon et al., 2005 IEEE Engineering in Medicine and Biology 27th Annual Conference, 2005, and in "*An ultra low power pulse oximeter sensor based on compressed sensing*" by P. K. Baheti et al., 2009 Sixth International Workshop on Wearable and Implantable Body Sensor Networks, June 2009.

There is a motivation to improve current state of the art electronic systems and methods for non-invasive cuffless blood pressure estimation.

SUMMARY

Disclosed herein are systems and method for non-invasive, cuffless blood pressure estimation. The methods and systems disclosed herein allow for calculation of systolic and/or diastolic arterial blood pressure of a subject. According to an example embodiment, the electronic system can calculate blood pressure values with low power consumption. According to an example embodiment, the electronic system can reduce power consumption by reducing the number of photoplethysmogram (PPG) signal samples needed for calculating a pulse arrival time period (PAT) between an electrocardiogram (ECG) signal and a PPG signal.

According to an example embodiment, the electronic system can also reduce power consumption by reducing the number of times a light emitter in a PPG sensor module is triggered in order to generate PPG signal samples. According to an example embodiment, the electronic system can also reduce power consumption by determining an optimal PPG signal sample acquisition period. According to an example embodiment, the electronic system can be completely implemented in a wearable device with small form factor. According to an example embodiment, the electronic system neither requires a base station nor involves a complex reconstruction process.

According to an example embodiment, provided is an electronic system for estimating a subject's arterial blood pressure, the system including: a heartbeat detection module configured for receiving an ECG signal and detecting a QRS complex of the ECG signal; a PPG sensor module configured for triggering a light emitter, thereby generating a plurality of samples of a PPG signal; a blood pressure calculation module configured for receiving information about the detected QRS complexes and the PPG signal samples, and calculating at least one blood pressure value (e.g. systolic and/or diastolic blood pressure values) based on a PAT between the ECG and the PPG signal; where the PPG sensor module is further configured for (i) receiving information about the detected QRS complexes, (ii) triggering, each time a QRS complex is detected, the generation of a plurality of samples of a PPG signal, and (iii) determining a PPG signal acquisition period.

According to an example embodiment, the PPG sensor module is configured for triggering the light emitter according to an uniform stimulation pattern, thereby generating a number of uniform samples of the PPG signal during said determined PPG acquisition period.

According to an example embodiment, the determined PPG signal acquisition period starts when a QRS complex is detected.

According to an example embodiment, the determined PPG signal acquisition period starts when an R peak is detected.

According to an example embodiment, the determined PPG signal acquisition period is determined as a time period that is smaller than an average RR interval.

According to an example embodiment, the determined PPG signal acquisition period is determined as a time period that is half of an average RR interval.

According to an example embodiment, the determined PPG signal acquisition period is dynamically calculated based on a plurality of heart beat intervals.

According to an example embodiment, the determined PPG signal acquisition period is determined based on a sum of sample slopes.

According to an example embodiment, the determined PPG signal acquisition period is determined to finish when the sum of the sample slopes reaches a predetermined threshold.

According to an example embodiment, the determined PPG signal acquisition period is further determined based on the duration of a plurality of previously determined PPG signal acquisition periods.

According to an example embodiment, the determined PPG signal acquisition period is determined based on a linear or non-linear combination of the duration of a predetermined number of previously determined PPG signal acquisition periods.

The disclosure also relates to an electronic device including a system for estimating a subject's arterial blood pressure according to embodiments described herein.

The disclosure also relates to a method for estimating a subject's arterial blood pressure. The method involves:

receiving a subject's ECG signal and detecting a QRS complex of said ECG signal; generating a plurality of samples of a PPG signal; receiving information about the detected QRS complexes and the PPG signal samples; and calculating at least one blood pressure value based on a PAT between the ECG signal and the PPG signal, where the step of generating a plurality of samples of a PPG signal involves triggering, each time a QRS complex is detected, the generation of a plurality of samples of a PPG signal during a determined PPG signal acquisition period.

The disclosure also relates to a computer program product including computer program code means adapted to calculate a subject's blood pressure according to the methods herein described when said program is run on a computer, and to a computer readable storage medium including such computer program.

According to an example embodiment, provided is an ECG assisted BP estimation, enabling ECG assisted PPG acquisition for cuffless blood pressure monitoring.

While current systems report achieving sufficient accuracy in determining BP for wearable applications, their power consumption is dominated by the PPG system, perhaps due to the uniform stimulation and sampling. Some current systems use Compressed Sampling based PPG for cuffless BP estimation. However, such systems employ a full signal reconstruction process to perform BP determination from the reconstructed PPG signal, with the assumption of the availability of a powerful base station. The overhead in the reconstruction process can potentially cancel all power savings obtained from CS acquisition of PPG.

According to an example embodiment, provided is an event driven approach that relies on assistance from ECG to acquire PPG. Realizing that the peak in PPG signal is the after effect of the pumping action of blood through vessels by heart, the occurrence of the QRS complex can be utilized to trigger the capture of the PPG signal. The acquisition can be stopped when a sufficient number of samples are acquired around the peak of the PPG signal. The presence of QRS complexes in the ECG can easily be detected using an activity detection process as outlined in "*A 17nA, 47.2 dB dynamic range, adaptive sampling controller for online data rate reduction in low power ECG systems*" by V. R. Pamula et al., 2016 IEEE Biomedical Circuits and Systems Conference (BioCAS), October 2016, pp. 272-275. A number of PPG acquisition stopping criteria are then determined for the PPG sampling including thresholding, sum-of-slopes, learning approaches and/or a combination thereof.

According to an example embodiment, since, the relative timing information of interest is completely preserved in the ECG assisted acquisition mode, both SBP and DBP are estimated with the same degree of accuracy as in the case of a continuous uniform sampling generation mode.

According to an example embodiment, the methods disclosed herein retain the relevant relative timing information between the ECG and the PPG signals, while facilitating accurate BP estimation at a reduced average stimulation and sampling rate.

According to an example embodiment, the proposed technique can provide more accurate results and can reduce more power consumption depending on the relative placement of the ECG and the PPG sensors.

BRIEF DESCRIPTION OF THE FIGURES

The above and other aspects of the system and method according to the present description will be shown and explained with reference to the non-restrictive example embodiments described hereinafter.

DETAILED DESCRIPTION

In the following, in the description of example embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the invention, as would be clearly understood by those skilled in the art. Additionally, in other instances, well-known methods, structures and techniques have not been shown in detail in order not to obscure the conciseness of the description.

Figure 1A:
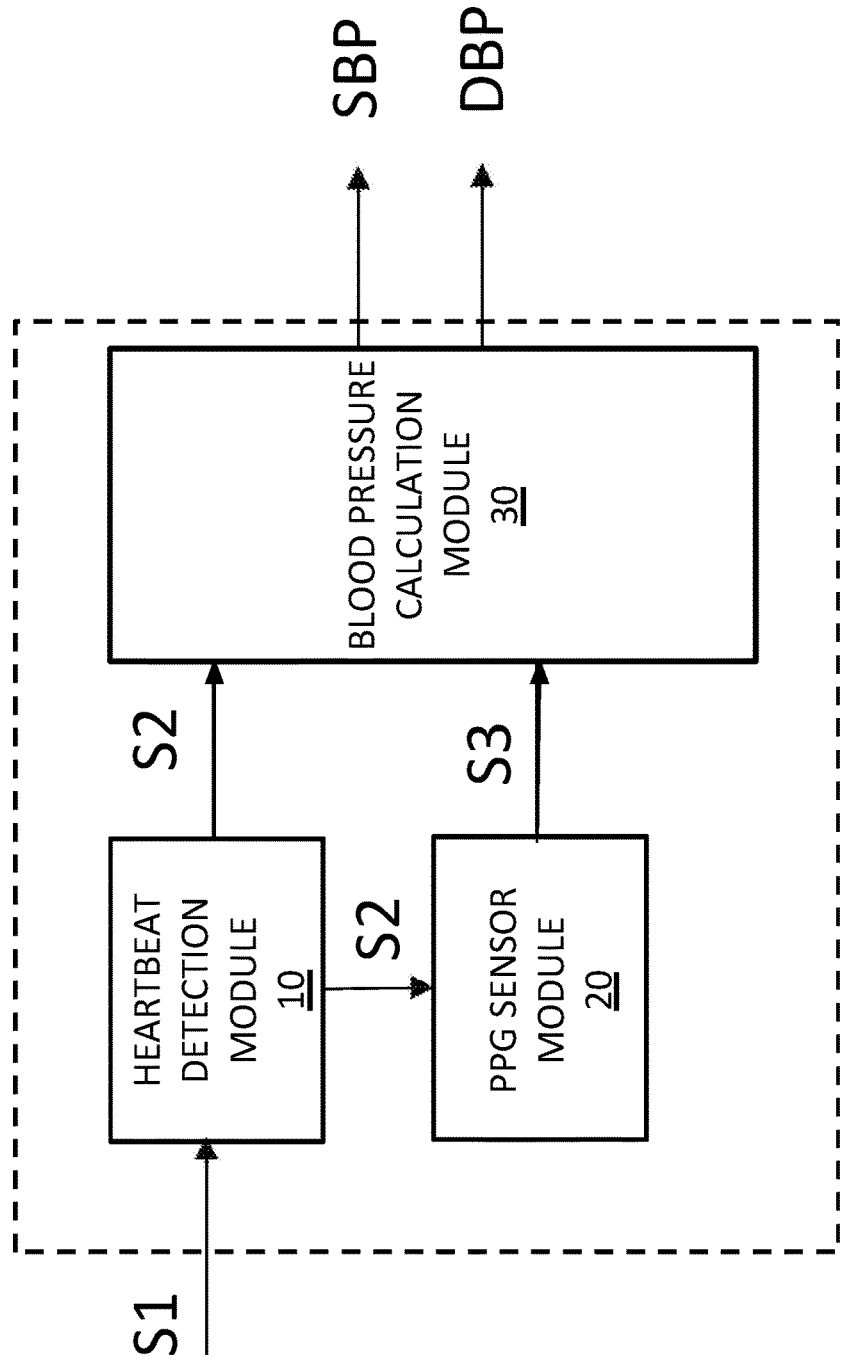
FIG. 1A illustrates a first general block diagram of an example system for blood pressure estimation, according to an example embodiment.
Figure 1B:
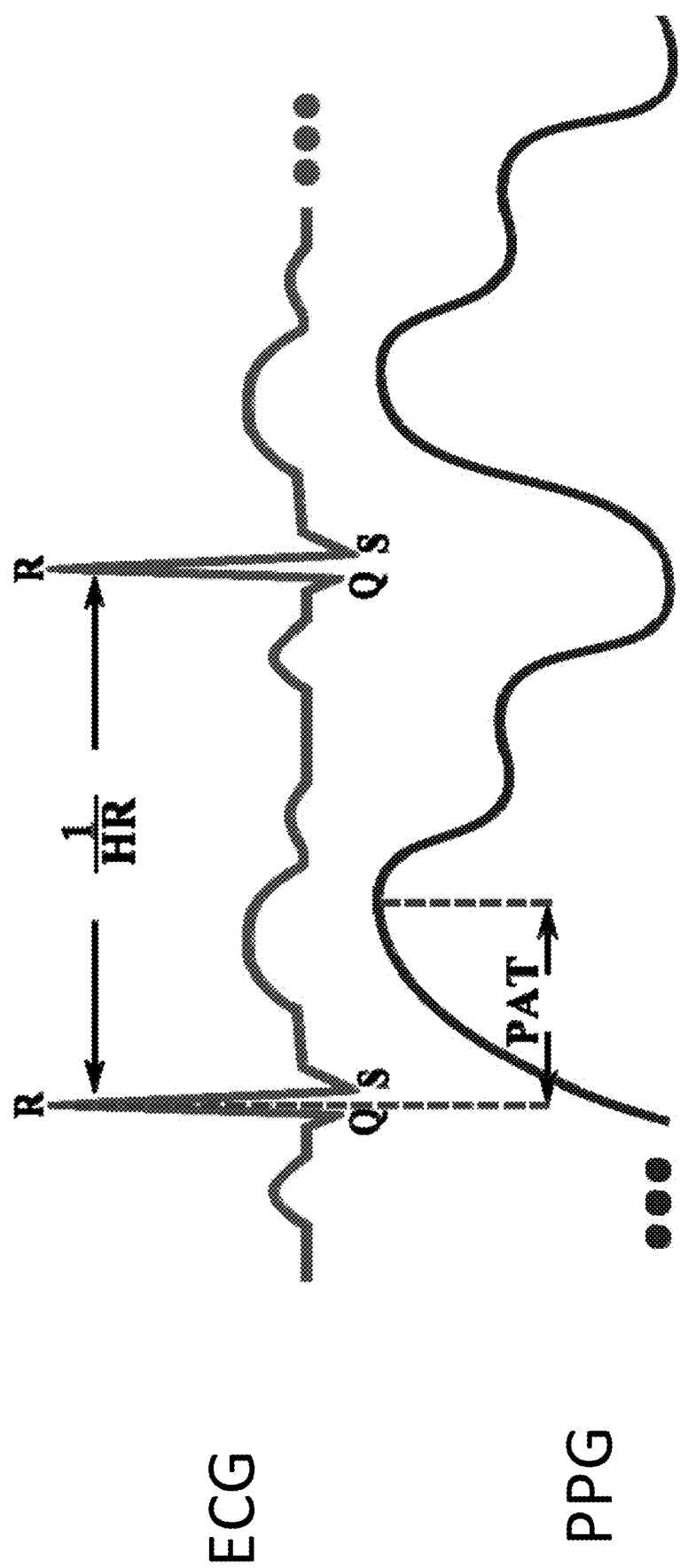
FIG. 1B illustrates a pulse arrival time period (PAT) between an ECG and a PPG signal, according to an example embodiment.

FIG. 1A shows a first general block diagram of an example system 100 for blood pressure estimation, according to an example embodiment. As shown in FIG. 1A, the system 100 includes a heartbeat detection module 10 configured for receiving an electrocardiogram signal S1 and detecting a QRS complex of said electrocardiogram signal. The system also includes a PPG sensor module 20 configured for triggering a light emitter and thereby generating a plurality of samples of a PPG signal S3. Further, the system 100 includes a blood pressure calculation module 30 configured for receiving information about the detected QRS complexes S2 and the PPG signal samples S3, and calculating at least one blood pressure value (e.g., SBP and DBP) based on a pulse arrival time period between the ECG and the PPG signal (as illustrated in FIG. 1B).

In an embodiment, the determination of BP is based on the relative timing between peaks in the ECG and PPG signals. FIG. 1B shows the relevant timing information required for the BP estimation. Of interest is the pulse arrival time (PAT), which is the temporal difference between the peak in the ECG to the subsequent peak in the PPG signal. Once the PAT is determined, BP can be estimated using the following equations:

$$SBP = a1\_PAT + b1\_HR + c1$$

$$DBP = a2\_PAT + b2\_HR + c2$$

where SBP and DBP are the systolic and diastolic blood pressure respectively, and where ai, bi and ci, for i=1, 2 are the calibration coefficients obtained through linear regression.

According to an example embodiment, the PPG sensor module 20 is further configured for (i) receiving information about the detected QRS complexes S2, (ii) triggering, each time a QRS complex is detected, the generation of a plurality of samples of a PPG signal, (iii) and determining a PPG signal acquisition period.

Figure 2:
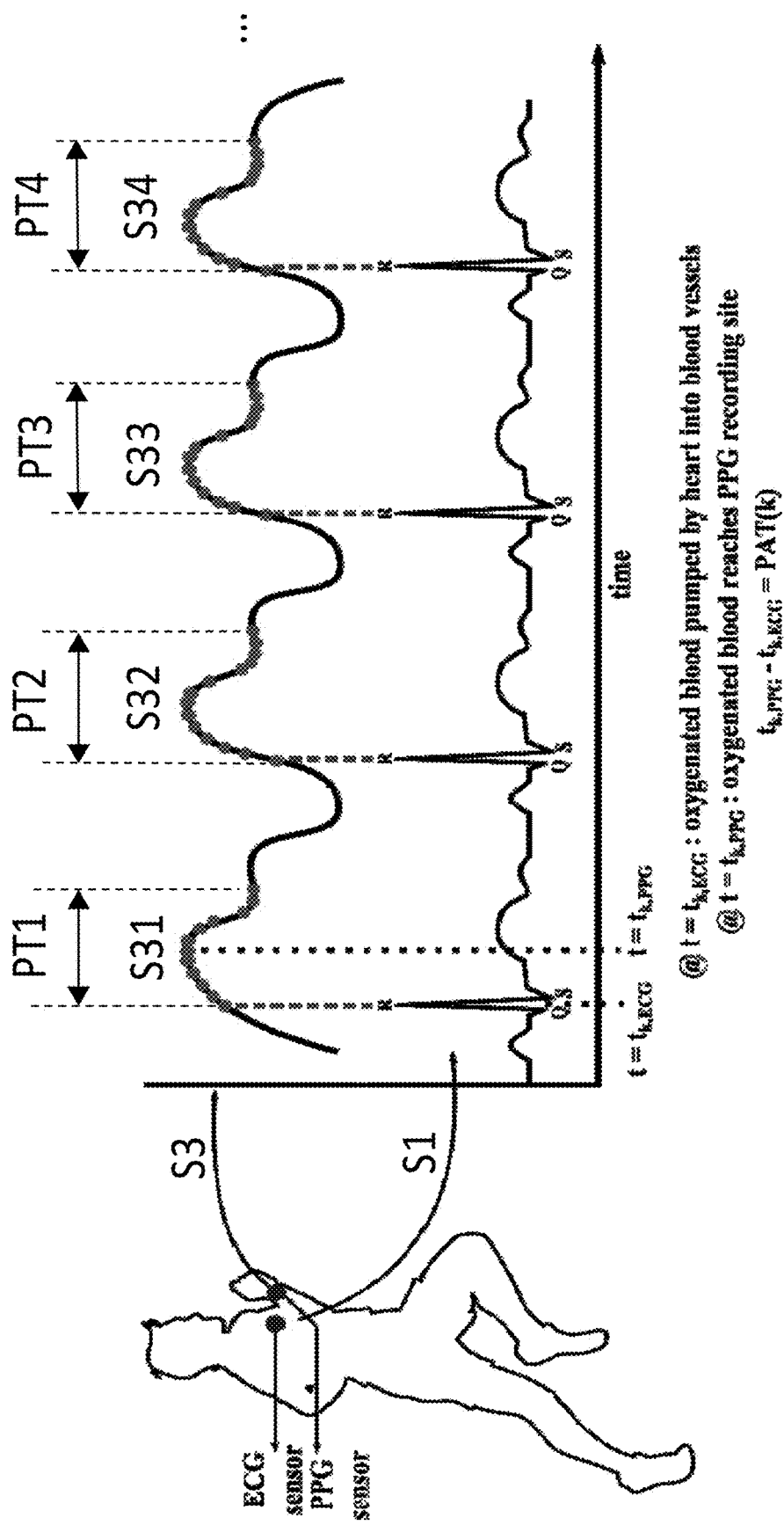
FIG. 2 shows an example of generated PPG signal samples and determined PPG acquisition periods based on ECG QRS signal detection and triggering, according to an example embodiment.
Figure 3:
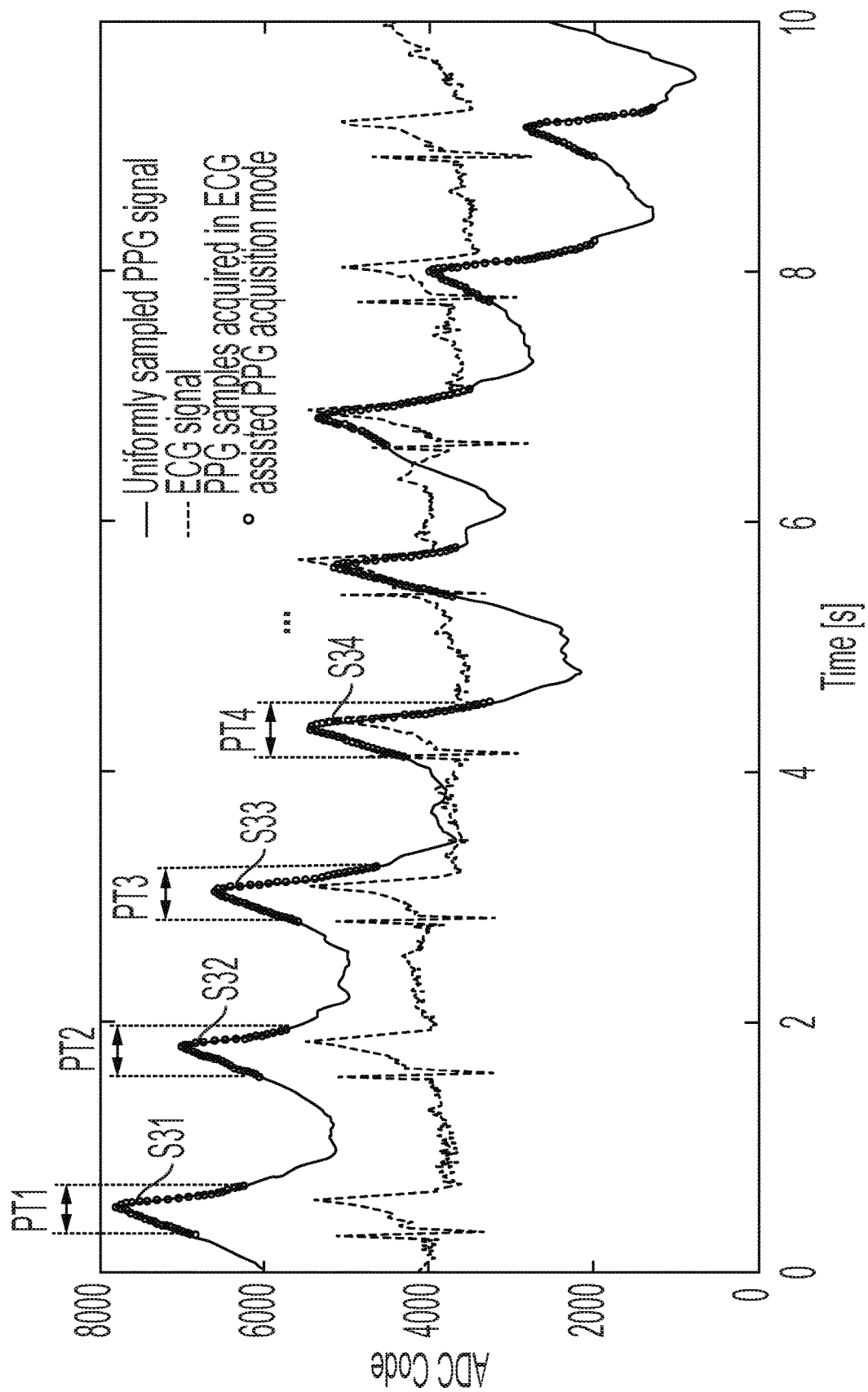
FIG. 3 shows another example of PPG samples acquired in ECG assisted PPG acquisition mode, according to an example embodiment.

FIGS. 2 and 3 show examples of generated PPG signal samples S31 to S34 and determined PPG acquisition periods PT1 to PT4 based on ECG QRS signal detection and triggering. According to an example embodiment, the PPG sensor module 20 is configured for triggering the light emitter, e.g. a LED, according to an uniform stimulation pattern, thereby generating a number of uniform samples (the dots in the sets of PPG samples S31 to S34 in FIG. 2 and the circumferences in the sets PPG of samples S31 to S34 in FIG. 3) of the PPG signal during each determined PPG acquisition period PT1 to PT4. According to an example embodiment, the PPG signal acquisition periods start when a QRS complex, e.g. an R peak in the ECG signal, is detected. According to an example embodiment, the PPG signal acquisition periods may be fixed or variable, depending on the PPG acquisition stopping criteria applied in the PPG sensor module 20.

Figure 4:
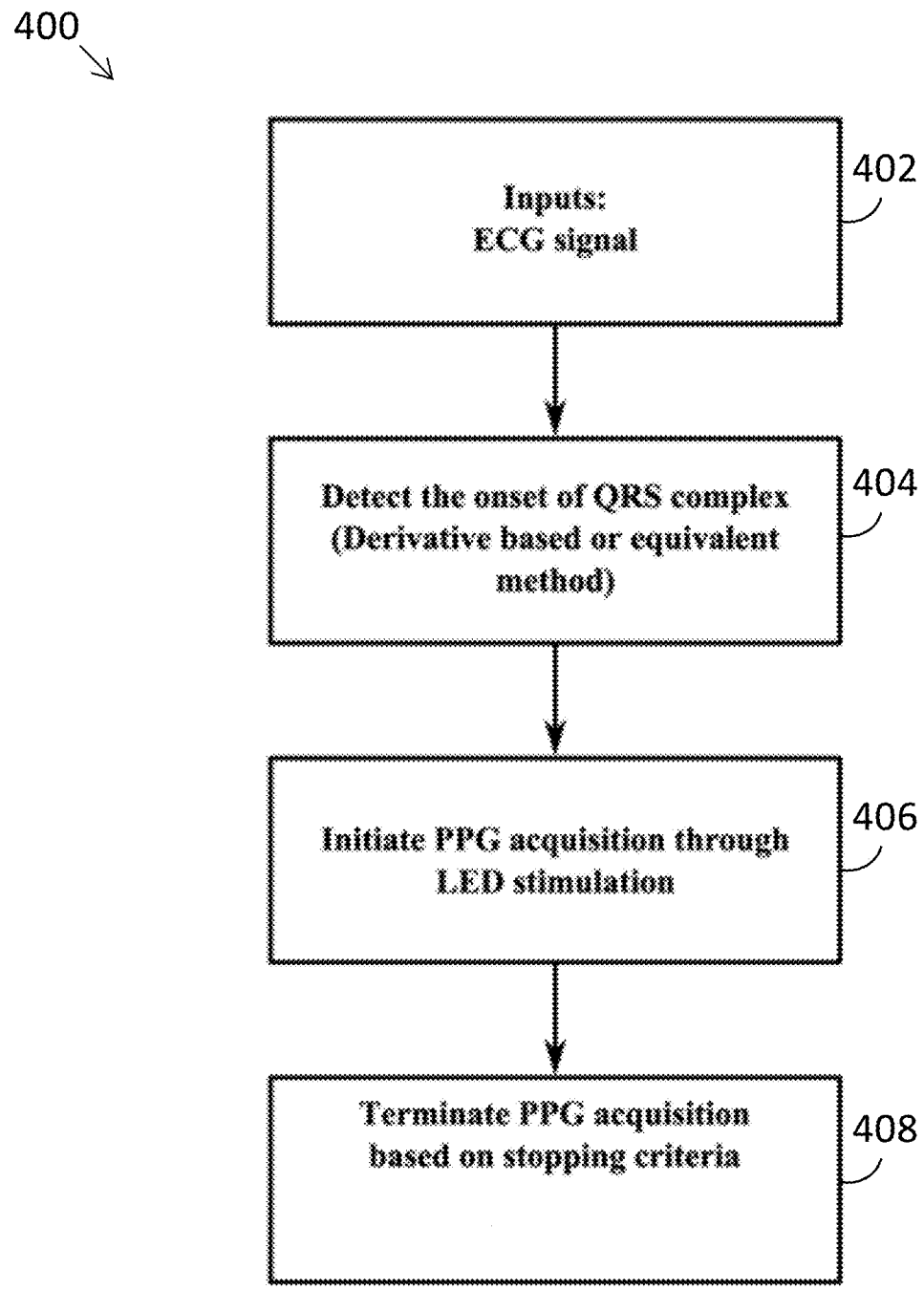
FIG. 4 shows a flow diagram for determining the PPG signal acquisition period and acquisition flow, according to an example embodiment.

FIG. 4 illustrates a flow diagram 400 for determining the PPG signal acquisition period and acquisition flow, according to an example embodiment. As shown by block 402, the input for determining the PPG signal acquisition period and acquisition flow is an ECG signal. As shown by block 404, the onset of a QRS complex (e.g., derivative based or equivalent method) is then detected. As shown by block 406, when the QRS complex is detected, the PPG acquisition is initiated, e.g. by stimulating the LED in the PPG sensor module 20, so that uniform PPG samples are generated and provided to the blood pressure calculation module 30. As shown by block 408, the PPG acquisition period is finished based on stopping criteria. Within examples, the stopping criteria can be fixed or can be determined dynamically.

According to an example embodiment, a method for estimating a subject's arterial blood pressure involves: receiving a subject's ECG signal and detecting a QRS complex of said ECG signal. The method also involves generating a plurality of samples of a PPG signal. Further, the method involves receiving information about the detected QRS complexes S2 and the PPG signal samples, and calculating at least one blood pressure value based on a PAT between the ECG signal and the PPG signal. The step of generating a plurality of samples of a PPG signal involves triggering, each time a QRS complex is detected, the generation of a plurality of samples S31 to S34 of a PPG signal during a determined PPG signal acquisition period PT1 to PT4.

Figure 5:
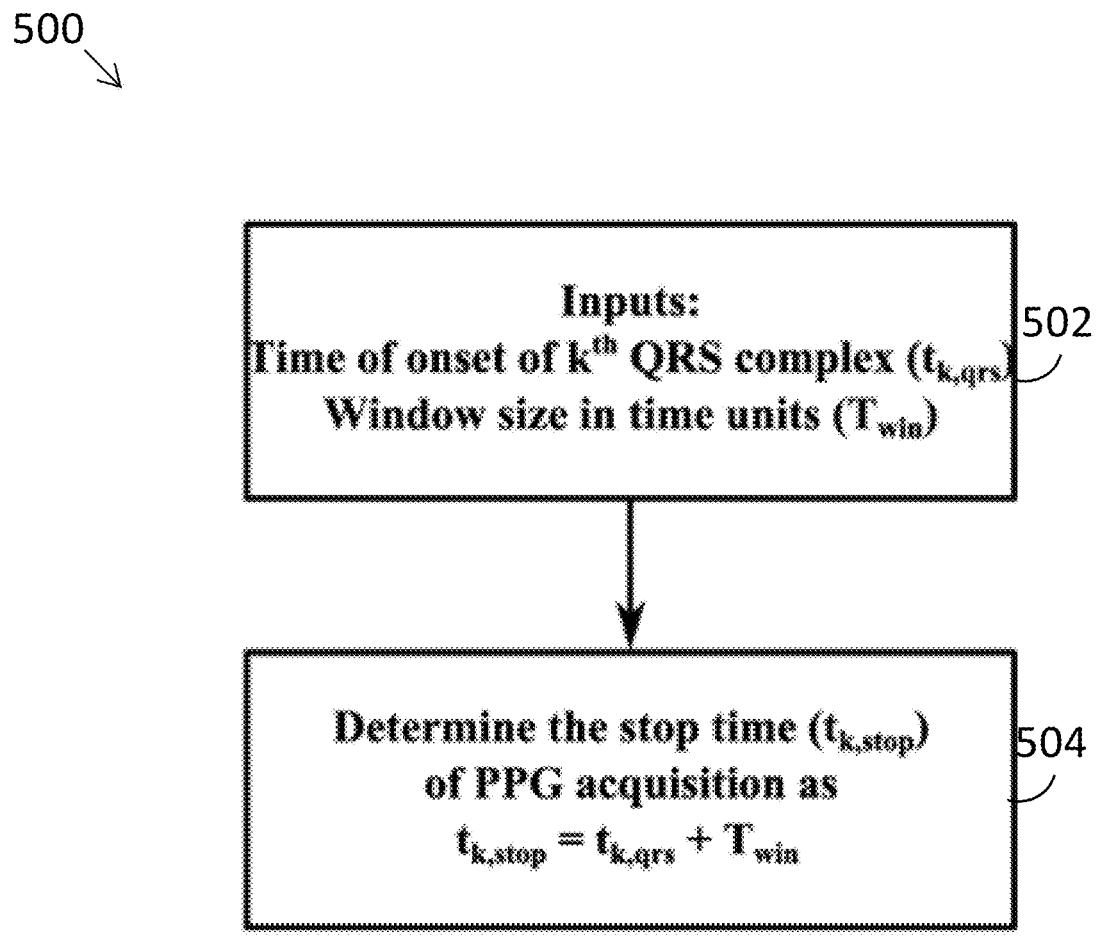
FIG. 5 shows another flow diagram for determining the PPG signal acquisition period, according to an example embodiment.

FIG. 5 shows another flow diagram 500 for determining the PPG signal acquisition period, according to an example embodiment. As shown by block 502, the input for determining the PPG signal acquisition period is a time of onset of the $k^{th}$ QRS complex ($t_{k,qrs}$) and a window size in time units ($T_{win}$). As shown by block 504, the stop time ($t_{k,stop}$) is then determined using the equation $t_{k,stop}=t_{k,stop}+T_{win}$.

According to an example embodiment, the determined PPG signal acquisition period is determined as a time period that is smaller than an average RR interval. According to an example embodiment, the determined PPG signal acquisition period is determined as a time period that is half of an average RR interval. According to an example embodiment, the determined PPG signal acquisition period may be a fixed or a variable time period. According to an example embodiment, the determined PPG signal acquisition period may be dynamically calculated based on a plurality of heart beat RR intervals or HR information.

Figure 6:
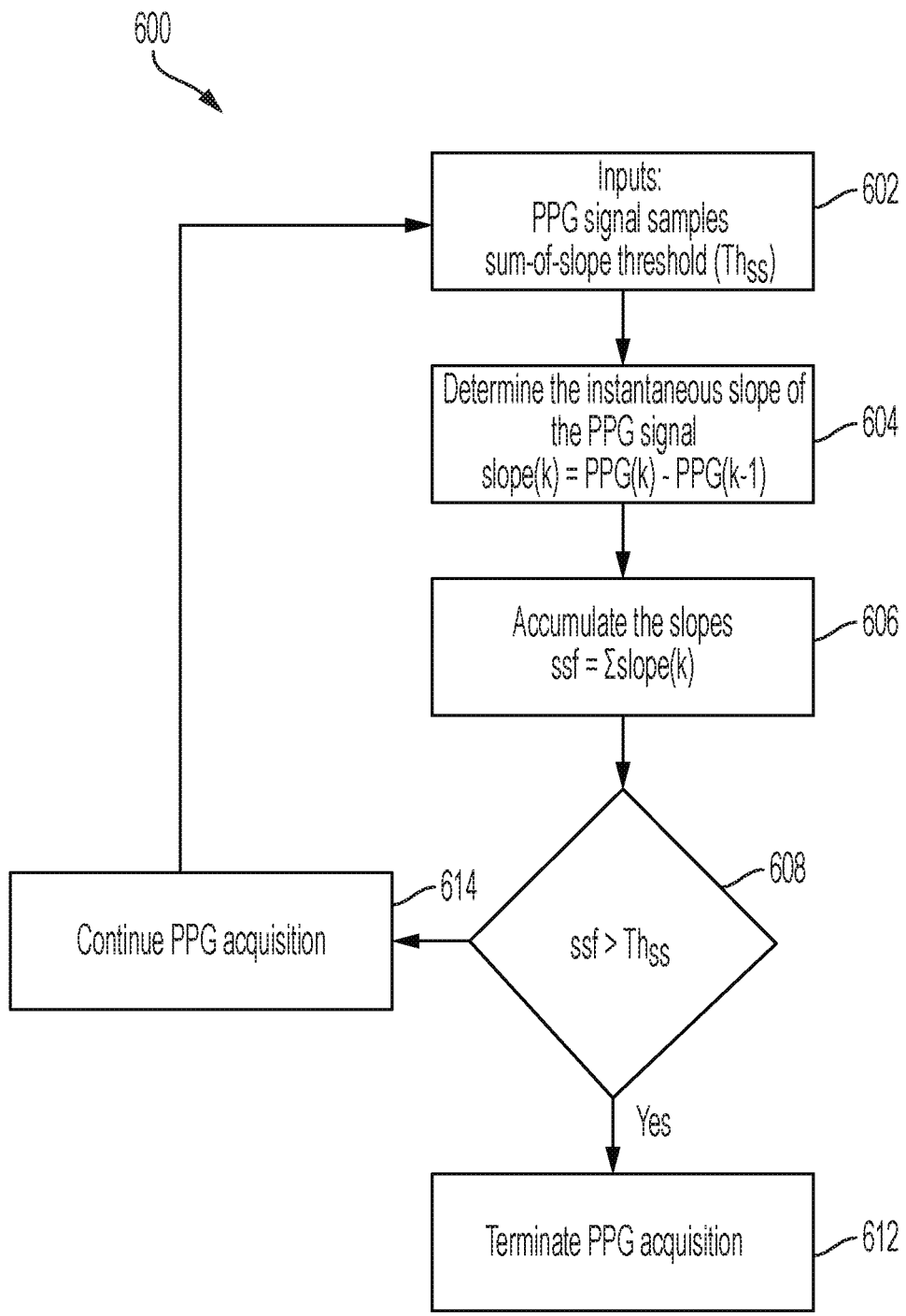
FIG. 6 shows a flow diagram for determining the PPG signal acquisition period with a sum of slopes stopping criteria, according to an example embodiment.

FIG. 6 shows a flow diagram for determining the PPG signal acquisition period with a sum of slopes stopping criteria, according to an example embodiment. As shown by block 602 of the flow diagram, the inputs for determining the PPG acquisition period are PPG signal samples and a sum-of-slope threshold ($Th_{ss}$). As shown by block 604 of the flow diagram, the inputs can be used to determine the instantaneous slope of the PPG signal using the equation: slope (k)=PPG(k)−PPG(k−1). As shown by block 606, the slopes are then accumulated using the equation ssf=Σslope (k). According to an example embodiment, the PPG signal acquisition will continue as long as the sum of the instantaneous slopes of the PPG samples is greater than a certain threshold. Conversely, if the sum of the instantaneous slopes of the PPG samples is less than a certain threshold, then the PPG acquisition will be terminated. Note that this is merely an example, and further stopping criteria can be generated based on the sum of the slopes of the generated PPG samples. This PPG signal acquisition period determination takes into consideration the form of the PPG signal and allows for more accurate results.

Figure 7:
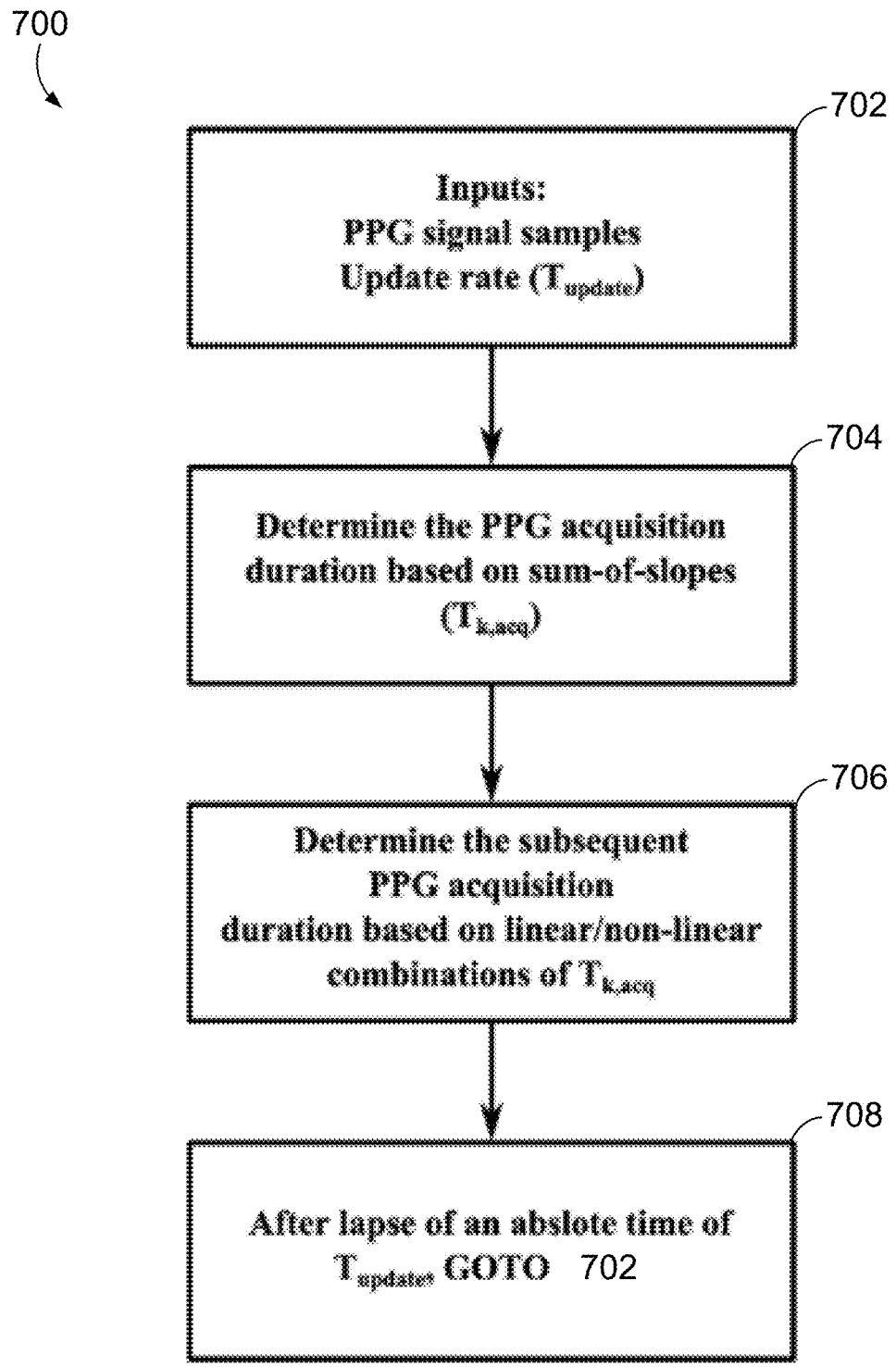
FIG. 7 shows a flow diagram for determining the PPG signal acquisition period with a learning based stopping criteria, according to an example embodiment.

FIG. 7 shows a flow diagram for determining the PPG signal acquisition period with a learning based stopping criteria, according to an example embodiment. As shown by block 702, the inputs for determine the PPG acquisition period with a learning based stopped criteria are the PPG signal samples and an update rate ($T_{update}$). As shown by block 702, the PPG acquisition duration is then determined based on the sum-of-slopes ($T_{k,acq}$). As shown by block 704, the subsequent PPG acquisition duration is determined based on linear/non-linear combinations of $T_{k,acq}$. As shown by block 706, after lapse of an absolute time of $T_{update}$, the flowchart returns to step 702.

According to an example embodiment, the determined PPG signal acquisition period may be further determined based on the duration of a plurality of previously determined PPG signal acquisition periods. According to an example embodiment, the determined PPG signal acquisition period is determined based on a linear or non-linear combination of the duration of a predetermined number of previously determined PPG signal acquisition periods.

It shall be noted that the system 100 for blood pressure estimation according to embodiments of the invention may be implemented according to hardware and/or software state of the art techniques, comprising for example a microprocessor, microcontroller or digital signal processor that can understand and execute software program instructions. Some programmable hardware logic and memory means may be specifically designed also for executing the method or parts of it according to example embodiments of the invention.

What is claimed is:

1. An electronic system for estimating arterial blood pressure comprising:
   a heartbeat detection module configured to (E) receive an electrocardiogram signal, and
   (ii) detect one or more QRS complexes of the electrocardiogram signal;
   a photoplethysmographic sensor module configured to trigger a light emitter, thereby generating a plurality of samples of a photoplethysmographic signal; and a blood pressure calculation module configured to (i) receive information about the one or more detected QRS complexes and the plurality of photoplethysmographic signal samples, and (ii) calculate at least one blood pressure value based on a pulse arrival time period (PAT) between the electrocardiogram and the photoplethysmographic signal, wherein the photoplethysmographic sensor module is further configured to (i) receive information about the one or more detected QRS complexes, (ii) trigger, each time a QRS complex is detected, the generation of the plurality of photoplethysmographic signal samples, and (iii) determine a photoplethysmographic signal acquisition period, and wherein during a first plurality of cycles of the photoplethysmographic signal, the photoplethysmographic sensor module is configured to:

determine, from samples of the photoplethysmographic signal taken during each cycle, a plurality of discrete time-varying slopes of the photoplethysmographic signal;

accumulate the discrete time-varying slopes;

compare the accumulated time-varying slopes with a threshold to thereby determine an acquisition duration associated with the cycle to facilitate calculating the at least one blood pressure value based on the PAT between the electrocardiogram and the photoplethysmographic signal.

2. The system of claim 1, wherein the photoplethysmographic sensor module is configured to trigger the light emitter according to a uniform stimulation pattern, thereby generating a number of uniform samples of the photoplethysmographic signal during the determined photoplethysmographic acquisition period.

3. The system of claim 1, wherein the determined photoplethysmographic signal acquisition period starts when a QRS complex is detected.

4. The system of claim 3, wherein the determined photoplethysmographic signal acquisition period starts when an R peak of the QRS complex is detected.

5. The system of claim 1, wherein the determined photoplethysmographic signal acquisition period is determined as a time period that is smaller than an average RR interval.

6. The system of claim 5, wherein the determined photoplethysmographic signal acquisition period is determined as a time period that is half of an average RR interval.

7. The system of claim 1, wherein the determined photoplethysmographic signal acquisition period is dynamically calculated based on a plurality of heart beat intervals.

8. The system of claim 1, wherein the determined photoplethysmographic signal acquisition period is determined to finish when the sum of the sample slopes reaches a predetermined threshold.

9. The system of claim 1, wherein the determined photoplethysmographic signal acquisition period is further determined based on a duration of a plurality of previously determined photoplethysmographic signal acquisition periods.

10. The system of claim 9, wherein the determined photoplethysmographic signal acquisition period is determined based on at least one of a linear or a non-linear combination of the duration of a predetermined number of the previously determined photoplethysmographic signal acquisition periods.

11. An apparatus for estimating a subject's arterial blood pressure comprising:

a heartbeat detection module configured to (i) receive an electrocardiogram signal, and (ii) detect one or more QRS complexes of the electrocardiogram signal;

a photoplethysmographic sensor module configured to trigger a light emitter, thereby generating a plurality of samples of a photoplethysmographic signal; and a blood pressure calculation module configured to (i) receive information about the one or more detected QRS complexes and the plurality of photoplethysmographic signal samples, and (ii) calculate at least one blood pressure value based on a pulse, arrival time period (PAT) between the electrocardiogram and the photoplethysmographic signal, wherein the photoplethysmographic sensor module is further configured to (i) receive information about the one or more detected QRS complexes, (ii) trigger, each time a QRS complex is detected, the generation of the plurality of photoplethysmographic signal samples, and (Hi) determine a photoplethysmographic signal acquisition period, wherein during a first plurality of cycles of the photoplethysmographic the photoplethysmographic sensor module is configured to:

determine, from samples of the photoplethysmographic signal taken during each cycle, a plurality of discrete time-varying slopes of the photoplethysmographic signal;

accumulate the discrete time-varying slopes;

compare the accumulated time-varying slopes with a threshold to thereby determine an acquisition duration associated with the cycle to facilitate calculating the at least one blood pressure value based on the PAT between the electrocardiogram and the photoplethysmographic signal.

12. A method for estimating arterial blood pressure comprising:

receiving an electrocardiogram signal;

detecting one or more QRS complexes of the electrocardiogram signal;

responsive to detecting each of the one or more QRS complexes, generating a plurality of samples of a photoplethysmographic signal during a determined photoplethysmographic signal acquisition period; and calculating, based on information associated with the detected QRS complexes and the photoplethysmographic signal samples, at least one blood pressure value based on a pulse arrival time period (PAT) between the electrocardiogram signal and the photoplethysmographic signal, wherein generating the plurality of samples of a photoplethysmographic signal during the determined photoplethysmographic signal acquisition period comprises:

determining, during a first plurality of cycles the photoplethysmographic signal and from samples of the photoplethysmographic signal taken during each cycle, a plurality of discrete time-varying slopes of the photoplethysmographic signal;

accumulating the discrete time-varying slopes; and comparing the accumulated time-varying slopes with a threshold to thereby determine an acquisition duration associated with the cycle to facilitate calculating the at least one blood pressure value based on the PAT between the electrocardiogram and the photoplethysmographic signal.

13. The method of claim 12, wherein the determined photoplethysmographic signal acquisition period starts when a QRS complex is detected.

14. The method of claim 13, wherein the determined photoplethysmographic signal acquisition period starts when an R peak of the QRS complex is detected.

15. The method of claim 12, wherein the determined photoplethysmographic signal acquisition period is determined as a time period that is smaller than an average RR interval.

16. The method of claim 15, wherein the determined photoplethysmographic signal acquisition period is determined as a time period that is half of an average RR interval.

17. The method of claim 12, wherein the determined photoplethysmographic signal acquisition period is dynamically calculated based on a plurality of heart beat intervals.

18. A non-transitory computer-readable medium having stored thereon program instructions that when executed by a processor of a computing device, cause the computing device to perform operations comprising:
    receiving an electrocardiogram signal;
    detecting one or more QRS complexes of the electrocardiogram signal;
    responsive to detecting each of the one or more QRS complexes, generating a plurality of samples of a photoplethysmographic signal during a determined photoplethysmographic signal acquisition period; and
    calculating, based on information associated with the detected QRS complexes and the photoplethysmographic signal samples, at least one blood pressure value based on a pulse arrival time period (PAT) between the electrocardiogram signal and the photoplethysmographic signal, wherein generating the plurality of samples of a photoplethysmographic signal during the determined photoplethysmographic signal acquisition period comprises:
    determining, during a first plurality of cycles the photoplethysmographic signal and from samples of the photoplethysmographic signal taken during each cycle, a plurality of discrete time-varying slopes of the photoplethysmographic signal;
    accumulating the discrete time-varying slopes; and
    comparing the accumulated time-varying slopes with a threshold to thereby determine an acquisition duration associated with the cycle to facilitate calculating the at least one blood pressure value based on the PAT between the electrocardiogram and the photoplethysmographic signal.

19. The non-transitory computer-readable medium of claim 18, wherein the determined photoplethysmographic signal acquisition period starts when a QRS complex is detected.

* * * * *